United States Patent [19]

Baker et al.

[11] Patent Number: 4,675,335
[45] Date of Patent: Jun. 23, 1987

[54] SULFUR CONTAINING ALKENYLENYL SUBSTITUTED BENZOIC ACIDS AND PHENYL TETRAZOLES AND THEIR USE AS ANTI-ALLERGIC AGENTS

[75] Inventors: Stephen R. Baker, Camberley; William J. Ross, Lightwater, both of England

[73] Assignee: Lilly Industries Limited, London, England

[21] Appl. No.: 822,703

[22] Filed: Jan. 27, 1986

[30] Foreign Application Priority Data

Jan. 30, 1985 [GB] United Kingdom ............... 8502258

[51] Int. Cl.$^4$ ................... C07D 257/04; A61K 31/41; C07C 63/06
[52] U.S. Cl. .................................. 514/381; 514/550; 514/570; 548/252; 548/253; 560/18; 560/14; 562/432; 260/543 P
[58] Field of Search ............... 548/252; 514/381, 550, 514/570; 560/18, 14; 562/432; 260/947

[56] References Cited

FOREIGN PATENT DOCUMENTS 68739 1/1983 European Pat. Off. .
123543 10/1984 European Pat. Off. .

OTHER PUBLICATIONS

V. Prelog, et al., *Helv. Chim. Acta*, 27, 1209 (1944), (Chemical Abstracts 40:848(8) supplied as an English Abstract).
G. A. Russell, et al., *J. Org. Chem.*, 31(9), 2854 (1966).
S. Kano, et al., *J. C. S. Chem. Comm.*, 785 (1978).
Eberbach et al., *Chem. Ber.*, 114, 2979 (1981).
Eberbach et al., *Tetrahedron Letters*, (48), 4640 (1979).
Tamura et al., *Synthesis*, (10), 693 (1977).

*Primary Examiner*—Richard L. Raymond
*Assistant Examiner*—D. B. Springer
*Attorney, Agent, or Firm*—Robert A. Conrad; Leroy Whitaker

[57] ABSTRACT

Pharmaceutical compounds are described of the formula

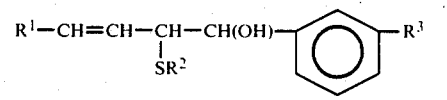

in which $R^1$ is (i) $R^4O(CH_2CH_2O)_n(CH_2)_m-$, where $R^4$ is hydrogen or $C_{1-5}$ alkyl, n is 0 or 1 to 5 and m is 1 to 7, or (ii) $R^5-X-$ where $R^5$ is a polar group and X is a $C_{6-20}$ alkylene or a $C_{6-20}$ alkenylene radical containing from 1 to 3 double bonds, $R^2$ is a group of the formula A—B— where A is —COOH or

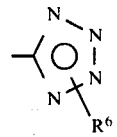

where $R^6$ is hydrogen or a protecting group, and B is $C_{1-6}$ alkylene, and $R^3$ is —COOH or

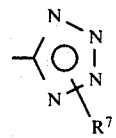

where $R^7$ is hydrogen or a protecting group; or a salt or ester thereof.

8 Claims, No Drawings

SULFUR CONTAINING ALKENYLENYL SUBSTITUTED BENZOIC ACIDS AND PHENYL TETRAZOLES AND THEIR USE AS ANTI-ALLERGIC AGENTS

This invention relates to novel compounds and their use as pharmaceuticals.

The compounds of the invention are of the formula

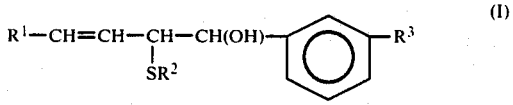

in which $R^1$ is (i) $R^4O$ $(CH_2CH_2O)_n(CH_2)_m$—where $R^4$ is hydrogen or $C_{1-5}$ alkyl, n is 0 or 1 to 5 and m is 1 to 7, or (ii) $R^5$—X— where $R^5$ is a polar group and X is a $C_{6-20}$ alkylene or a $C_{6-20}$ alkenylene radical containing from 1 to 3 double bond, $R^2$ is a group of the formula A—B— where A is —COOH or

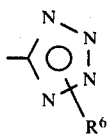

where $R^6$ is hydrogen or a protecting group, and B is $C_{1-16}$ alkylene, and $R^3$ is —COOH or

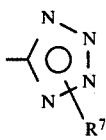

where $R^7$ is hydrogen or a protecting group; and salts and esters thereof.

The compounds of the invention, with the exception of compounds in which $R^6$ or $R^7$ is a protecting group which are intermeidates in the preparation of the remaining compounds, are pharmacologically active in tests which demonstrate their antagonist effect on leukotriene receptors and indicate their use in the treatment of allergic disorders.

When reference is made to "$C_{1-5}$ alkyl" herein, the radical can be straight-chain or branched and preferred examples include methyl, ethyl, propyl, isopropyl or butyl, most preferably "$C_{1-5}$ alkyl" is methyl or ethyl.

When $R^1$ is a polyether group of the formula $R^4O$ $(CH_2CH_2O)_m(CH_2)_n$—, m can be 0 or take a value of 1 to 5 and n takes the value of 1 to 7. Preferably m is 2 to 4 and n is 1 to 3. The value of $R^4$ is preferably $C_{1-5}$ alkyl such as methyl or ethyl.

When $R^1$ is of the formula $R^5$—X—, $R^5$ can be any conventional polar group. Examples include groups of the formula —$COR^8$ where $R^8$ is —OH or —$NR^9R^{10}$ where $R^9$ and $R^{10}$ are hydrogen, $C_{1-5}$ alkyl or together with the nitrogen atom, form a heterocyclic ring such as a morpholino, piperidino or pyrrolidino ring. Alternatively the polar group can be —OH, —$NH_2$, tetrazolyl, or a sulphonate or phosphonate derivative, —$SO_3H$ or —$PO_3H_2$ respectively. Salts and esters of such polar groups are also included and preferred polar groups are of the formula —OH or —$COR^8$ where $R^8$ is —OH or —$NR^9R^{10}$ where $R^9$ and $R^{10}$ are each hydrogen or $C_{1-4}$ alkyl.

With regard to the group $R^5$—X—, the X radical can be $C_{6-20}$ alkylene or $C_{6-20}$ alkenylene containing 1 to 3 double bonds. When X is alkylene, it is preferably straight-chain and of the formula —$(CH_2)_p$— where p is 6 to 20, more particularly 8 to 15. Thus preferred examples of $R^5$—X— are of the formula $HO(CH_2)_p$— or $R^8CO(CH_2)_p$— where $R^8$ is —OH or —$NR^9R^{10}$ where $R^9$ and $R^{10}$ are hydrogen or $C_{1-4}$ alkyl, and p is 8 to 15. When X is alkenylene, it is preferably straight-chain and of the formula —$(CH_2)_q$—CH=CH— or —$(CH_2)_r$CH=CHCH$_2$(CH=CH)$_2$— where q is 6 to 12 and r is 2 to 8. Thus especially preferred examples of $R^5$—X— are of the formulae $HO(CH_2)_q$—CH=CH— and $R^8CO(CH_2)_q$—CH=CH— where $R^8$ is —OH. Particularly preferred examples of $R^1$ are $HOCH_2(CH_2)_7CH_2CH$=CH— and $HO_2C(CH_2)_7CH_2CH$=CH—.

It will be appreciated that the double bonds in the $R^1$ group, and the double bond between the 3 and 4 carbon atoms, provide opportunities for cis-trans isomeric forms. It is preferred that the $R^1$ group is arranged in trans configuration about the double bond at the 3 and 4 carbon atoms. It will also be appreciated that the compounds of formula (I) possess chiral centres at the carbon atoms bearing the hydroxyl and thio groups and, accordingly, stereoisomeric forms exist R,R; S,S; R,S; and S,R. All such stereoisomers, and racemic mixtures thereof, are included within the scope of the invention. The preferred compounds are of S,R configuration. Isomers can be isolated from racemic mixtures by conventional methods such as by the preparation of diastereoisomers with subsequent liberation of the enantiomers or, alternatively, can be prepared by methods devised to give the pure isomer.

The $R^2$ group in formula (I) comprises an alkylene group, "A", having 1 to 6 carbon atoms which can be branched or unbranched and is preferably of the formula —$(CH_2)_s$— where s is 1, 2 or 3.

The groups A and $R^3$ are preferably tetrazolyl or protected tetrazolyl.

When $R^6$ or $R^7$ is a protecting group it can be any of the well known protecting groups employed for the purpose of protecting the tetrazolyl radical and such groups include optionally substituted trityl and benzhydryl, and optionally substituted benzyl for example p-methoxybenzyl or a silyl group for example t-butyldiphenylsilyl. As is well known the tetrazolyl group exhibits tautomerism and the position of attachment of the protecing group will depend on its size, though generally the point of attachment is at the 2-position.

The compound of formula (I) can have acidic functions, when $R^6$ or $R^7$ is hydrogen, or when A or $R^3$ are —COOH, or when $R^5$ is an acidic function. Base addition salts of these compounds can thus be prepared and these are included as part of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms together with other pharmaceutically acceptable salts are particularly preferred, but it is to be understood that other non-pharmaceutical salts are included in the invention since they may be useful for identification, charactisation or purification of the free compound.

Similarly when one or more of the groups bears a —COOH radical, for example when $R^5$, A or $R^3$ is —COOH, esters can be formed, the preferred ones being those derived from alkanols containing 1 to 4 carbon atoms, especially the methyl and ethyl esters.

A particular group of compounds according to formula (I) above are those of the formula

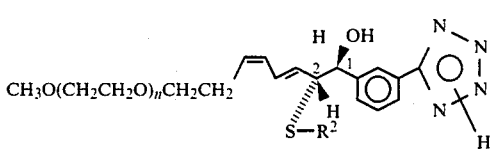

in which n is 2 or 3, $R^2$ is —(CH$_2$)$_s$—A where A is COOH or

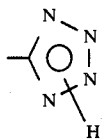

and s is 1, 2 or 3; and salts and esters thereof. Such compounds exhibit 1S,2R chirality.

A further group of compounds of especial interest are those of the formula

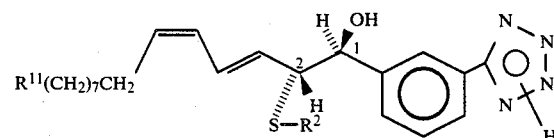

in which $R^{11}$ is —CH$_2$OH or —COOH or —CONR$^9$R$^{10}$ where $R^9$ and $R^{10}$ are hydrogen or C$_{1-4}$ alkyl, $R^2$ is —(CH$_2$)$_s$—A where A is —COOH or

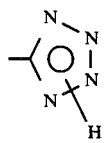

and s is 1, 2 or 3; and salts and esters thereof.

The invention also includes a process for producing a compound of general formula (I) which comprises reacting a compound of the formula

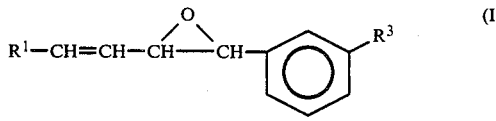    (II)

in which $R^1$ is as defined above and $R^3$ is —COOR$^{12}$ or

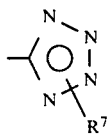

where $R^7$ is a protecting group and $R^{12}$ is an ester group, with a thiol of the formula

A—B—SH    (III)

where A and B have the values ascribed to them above, optionally followed by removal of an $R^6$ or $R^7$ protecting group or an $R^{12}$ ester group. The reaction is generally carried out in the presence of a base, preferably a strong base such as potassium t-butoxide in an inert organic solvent such as for example t-butanol at a temperature of from 0° C. to 60° C.

Intermediate compounds of formula (II) may be prepared by the Wittig reaction of a phosphonium salt of formula $R^{13}$CH$_2$P$^+$Ph$_3$Br$^-$, $R^{13}$ being an appropriate polyether or $R^5$—X—group, in the presence of a base such as butyl lithium, with an aldehyde of formula (IV) or (V)

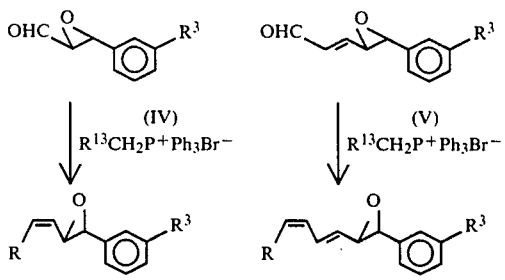

where $R^3$ is protected. The reaction is generally carried out in an inert organic solvent such as for example, tetrahydrofuran, at a temperature of from —110° C. to 0° C. The phosphonium reagents can be made from known compounds by standard routes. In the case of the polyether derivatives an alcohol, for example, triethylene glycol monomethyl ether can be reacted, in the presence of base such as potassium t-butoxide and t-butanol, with 1-bromo-3-chloropropane, to give an appropriate chloroderivative which on reaction with triphenylphosphine gives the desired reagent.

Compounds of formula (IV) may be prepared from known intermediates by, for example, two principal routes. Firstly, they may be prepared, as racemic mixtures, by oxidation with, for example, hydrogen peroxide and sodium hydrogen carbonate in methanolic solution, of an aldehyde of the formula

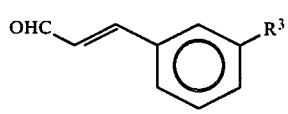

in which $R^3$ is a protected group and, in its turn, the aldehyde of formula (IV) may be converted to one of formula (V) by reaction with formylmethylanetriphenylphosphorane.

Alternatively, the compounds of formula (IV) may be prepared by oxidation of an epoxy alcohol of the formula

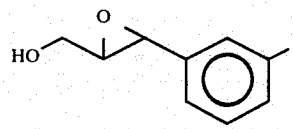
(VI)

with an oxidising agent such as, for example, chromium trioxide in pyridine. Compounds of formula (VI) can be prepared in stereospecific form, the steric configuration being retained on oxidation to provide the aldehyde of formulae (IV) and, ultimately, of formula (V).

Compounds of formula (VI) are prepared from the allyl alcohol

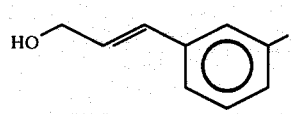
(VII)

using as epoxidising agent a reagent such as titanium isopropoxidet-t-butyl hydroperoxide in the presence of L or D diethyl tartrate which yields the S,S or R,R epoxide with the above E olefin. When the Z olefin is used as starting material, the appropriate S,R and R,S stereoisomers result. Compounds of formula (VII) can be prepared from the appropriate benzaldehyde via a sequence of reactions involving reaction with malonic acid to provide the cinnamic acid derivative, treatment with oxalyl chloride to give the acid chloride, and reduction with a reagent such as lithium tri-t-butoxyaluminohydride. The Z olefin is produced by catalytic reduction using a Lindlar catalyst of the appropriate acetylenic derivative.

Compounds of formula (III) can be prepared from the appropriate compound of formula A—B—Br by reaction with benzyl mercaptan to give a benzylthio nitrile which, in its turn, can be converted with azide and ammonium chloride to the corresponding tetrazolyl derivative from which the compound of formula (III) is liberated by treatment with sodium in liquid ammonia. A preferred method of making the compound in which —B— is —(CH$_2$)$_2$—is from acrylonitrile as starting point using the Michael reaction.

The following scheme shows how compounds of the invention may be prepared:

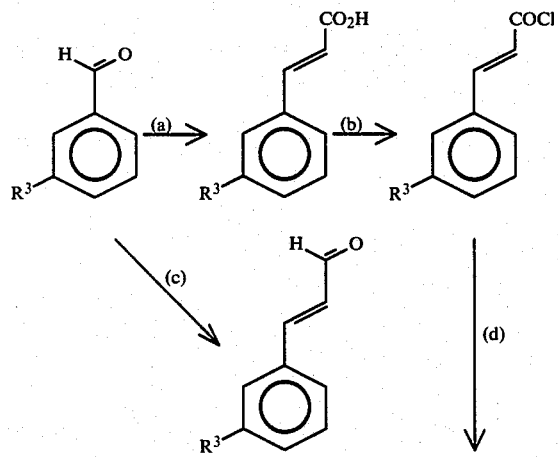

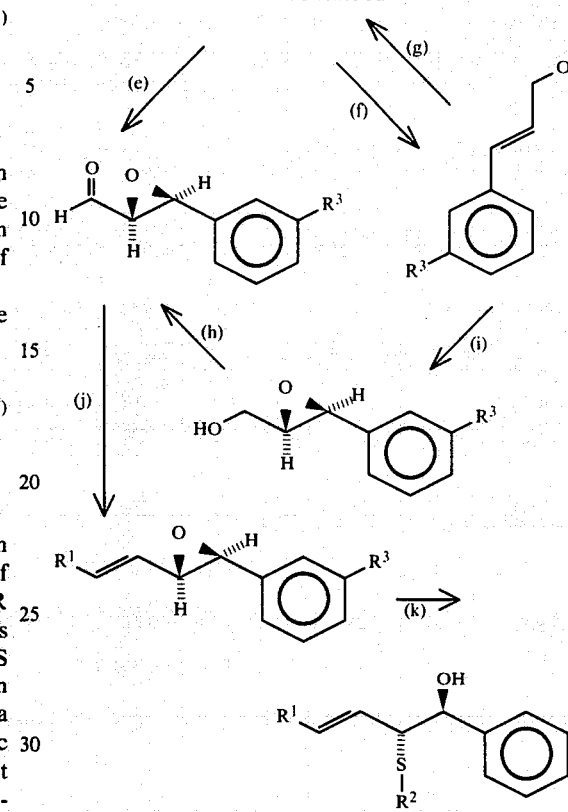

Key:
(a) reaction with malonic acid in pyridine and piperidine.
(b) reaction with oxalyl chloride in ether
(c) reaction with formylmethylenetriphenylphosphorane in toluene
(d) reaction with lithium tri-t-butoxyaluminohydride in tetrahydrofuran
(e) reaction with hydrogen peroxide and sodium hydrogen carbonate in methanolic solution
(f) reaction with sodium borohydride in methanol
(g) reaction with manganese dioxide in dichloromethane
(h) reaction with chromium oxide in pyridine
(i) reaction with titanium isopropoxide-t-butyl peroxide in dichloromethane and L-diethyl tartrate
(j) reaction with R$^1$CH$_2$P$^+$Ph$_3$Br$^-$ in the presence of butyl lithium and in tetrahydrofuran as solvent
(k) reaction with thiol of formula (III).

The compounds of the present invention are pharmacologically acitve, being leukotriene antagonists. They are active in the in vitro test on guinea pig ileum segments at concentrations of from 10 ng/ml, according to the method of Schild (1947) Brit. J. Pharm 2, 197-206 (the unprotected compounds of formula (I) exhibit an IC$_{50}$ against LTD$_4$ of less than 10$^{-5}$ molar). Also compounds of the invention are active in the in vivo Guinea Pig Pulmonary Function Test of Austen and Drazen (1947) J. Clin. Invest. 53 1679–1685 at intravenous dosage levels of from 0.05 μg to 5.0 mg/kg and in a modified "Herxheimer" test (Journal of Physiology (London) 117 251 (1952)) at doses of from 25 to 200 mg/kg. The "Herxheimer" test is based on an LTD$^4$- induced bronchospasm in guinea pigs which closely resembles an asthmatic attack in man.

The compounds are indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung and Pigeon Fanciers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and crystic fibrosis and rheumatic fever.

Thus the invention also includes a pharmaceutical composition comprising a pharmaceutically acceptable diluent or carrier in association with a compound of formula (I) in unprotected form; or a pharmaceutically acceptable salt or ester thereof.

The compounds may be administered by various routes, for examples by the oral or rectal route, topically or parenterally, for example by injection, and especially by inhalation, being usually employed in the form of a pharmaceutical composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 250 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The following compounds of the invention are prepared according to the method described above:
(1S,2R)-5-{3-[2-(2-Carboxyethylthio)-1-hydroxyhepta-(3E),(5,Z)-dienyl-7-(2-{2-methoxyethoxyethoxy}ethoxy)]phenyl}-1H-tetrazole.
(1S,2R)-5-{3-{2-[2-Carboxyethylthio]-1-hydroxyocta-(3E), (5Z)-dienyl-8-[2-(2-methoxyethoxy)ethoxy]{phenyl}-1H-tetrazole.
(1S,2R)-5-{3-{2-(2-1H-Tetrazol-5-ylethylthio]-1-hydroxyhepta-(3E), (5Z)-dienyl-7-[2-(2-methoxyethoxy)ethoxy]}phenyl}-1H-tetrazole.
(1S,2R)-3-{2-[2-Carboxyethylthio]-1-hydroxyhepta-(3E), (5Z)-dienyl-7-(2-methoxyethoxy)ethoxy]} phenylcarboxylic acid. (1S,2R)-5-{3-[14-Carboxy-2-(2carboxy-1-ethylthio)-1-hydroxytetradeca-(3E), (5Z)-dienyl]phenyl}-1H-tetrazole.
(1S,2R)-5-{3-[14-Carboxy-2-(2-{1H-tetrazol-5-yl}-1-ethylthio)-1-hydroxytetradeca-(3E), (5Z)-dienyl]phenyl}-1H-tetrazole.
(1S,2R)-5-{3-[15-Hydroxy-2-(2-carboyx-1-ethylthio)-1-hydroxypentadeca-(3E), (5Z)dienyl]phenyl}-1H-tetrazole.
(1S,2R)-5-{3-[15-Hydroxy-2-(2-{1H-tetrazol-5-yl}-1-ethylthio)-1-hydroxypentadeca-(3E),(5Z)-dienyl]phenyl}-1H-tetrazole.

Specific details of the preparation of compounds of the invention are given in the following Examples.

EXAMPLE 1

1-Chloro-3-{2-[2-(2-methoxyethoxy)ethoxy]ethoxy} propane

To a solution of triethyleneglycol monomethylester (16.42 g) and 1,3-bromochloropropane (31.4 g) in dry t-butanol (150 ml) was added potassium t-butoxide (12.3 g). The suspension was then stirred at 50° C. for 48 hours and the reaction followed by gas chromatography on an OV17 100–200 mesh column. The cooled reaction mixture was then distilled on a Kugelrohr. The product distilled at 110° C./0.7 mm as a clear colourless oil.

Similarly prepared was:
1-Chloro-3-[2-(2-methoxyethoxy)ethoxy]propane, 60° C./0.4 mm.

3- 2-[2-(2-Methoxyethoxy)ethoxy]ethoxy propyltriphenyl phosphonium iodide

To a solution of 1-chloro-3-{2-[2-(2-methoxyethoxy)ethoxy]ethoxy}propane (2.4 g) in dry acetonitrile (30 ml) was added potassium iodide (1.66 g), and triphenylphosphine (2.63 g) and the suspension heated at reflux for 24 hours. The cooled solution was filtered and the filtrate evaporated under reduced pressure to give a colourless oil which on cooling to −20° C. gave a white oily solid.

Similarly prepared was:
3-[2-(2-Methoxyethoxy)ethoxy]propyltriphenylphosphonium iodide.

5-{3-[1,2-Oxido-9,12,15,18-tetraoxanonadeca(3E),(5Z)-dienyl]-phenyl}-2-triphenylmethyltetrazole To a stirred suspension of 3-{2-[2-(2-methoxyethoxy)ethoxy]ethoxy}propyltriphenylphosphonium iodide (1.0 g) in dry tetrahydrofuran (40 ml) at −75° C. under nitrogen was added dropwise, n-butyl lithium in hexane (1.1 ml, 1.6M). The cloudy orange solution formed was stirred at −75° C. for 30 minutes, then a solution of 1-[3-(2-triphenylmethyltetrazol-5-yl)phenyl]-1,2-oxidopent-3-enal (800 mg) (see British Patent Application No. 2 144 422) in dry tetrahydrofuran (10 ml) was added dropwise and the pale yellow solution left to stir at −75° C. for 1 hour. The solution was allowed to warm to room temperature and evaporated under reduced pressure to give a brown oily solid. The solid was extracted with hot ether, the ether extract evaporated under reduced pressure to give a yellow brown oil which was chromatographed on a Sorbsil U30 column using ether to give a yellow oil.

Similarly prepared was:
5-{3-[1,2-Oxide-9,12,15-trioxahexadeca(3E),(5Z-)dienyl]phenyl}-2-triphenylmethyltetrazole.

(1S,2R)-5-{3-[2-(2-Methylcarboxyethylthio)-1-hydroxy-9,12,15,18-tetraoxanonadeca(3E),(5Z)dienyl]-phenyl}-2-triphenylmethyltetrazole A solution of the above epoxide (350 mg) in methanol (2 ml) was added, under nitrogen, to a stirred solution of methylthiopropionate (140 mg) and triethylamine (120 mg) in methanol (5 ml). The reaction mixture was left to stir at room temperature under nitrogen for 36 hours, evaporated under reduced pressure and chromatographed on a Sorbsil U30 column using ether, to give a pale yellow oil.

Similarly prepared was:
(1S,2R)-5-{3-[2-(2-Methylcarboxyethylthio)-1-hydroxy-9,12,15-trioxahexadeca(3E),(5Z)dienyl]-phenyl}-2-triphenylmethyltetrazole.

(1S,2R)-5-{3-[2-(2-Carboxyethylthio)-1-hydroxy-9,12,15,18-tetraoxanonadeca(3E),(5Z)dienyl]phenyl}-1H-tetrazole The above protected tetrazole (200 mg) was dissolved in diethylether (3 ml) to which was added aqueous formic acid (50%; 4 ml) and the mixture was left to stir at room temperature for 24 hours. The ether was evaporated under reduced pressure and tetrahydrofuran (5 ml) added. The mixture was then made basic with aqueous lithium hydroxide (2 N; 20 ml) and the solution left to stir at room temperature for a further 4 hours. The tetrahydrofuran was evaporated under reduced pressure, the residue made acidic with 2NHCl, extracted with ether (3×20 ml), dried over magnesium sulphate, filtered and evaporated under reduced pressure to give a pale yellow oil. The oil was chromatographed by HPLC on a LPI-ODS packed column using methanol:water:acetic acid (60:40:0.5) to give a colourless oil. NMR in CDCl3 in d4-methanol (80 MHz) gave confirmation of the structure.

Similarly prepared was:
(1S,2R)-5-{3-[2-(2-Carboxyethylthio)-1-hydroxy-9,12,15-trioxahexadeca(3E),(5Z)dienyl]phenyl}-1H-tetrazole.

NMR δ in CDCl3 (300 MHz): 2.41 (quartet, 2H), 2.66 (multiplet, 2H), 2.74 (multiplet, 2H), 3.32 (singlet, 3H), ~3.6 (multiplet, 10H), 3.85 (double doublet, 1H), 4.85 (doublet, 1H), 5.33 (doublet of triplets, 1H J=10 Hz), 5.57 (double doublet, 1H J=16 Hz), 6.00 (triplet, 1H J=10 Hz), 6.39 (double doublet, 1H J=16 Hz), ~7.5 (multiplet, 2H), 8.02 (multiplet, 1H), 8.19 (multiplet, 1H).

EXAMPLE 2

Methyl-10-bromodecanoate

A solution of 10-bromodecanoic acid (5 g) in methanol (60 ml) and concentrated sulphuric acid (3 drops) was refluxed for 20 hours.

The methanol was evaporated in vacuo, and the residual oil partitioned between water (50 ml) and dichloromethane (2×50 ml). The organic extracts were washed with 10% sodium carbonate (2×100 ml) and saturated brine (2×100 ml), and dried over magnesium sulphate and evaporated in vacuo to give the required product as a nearly colourless oil.

9-(Methoxycarbonyl)-nonyl-triphenyl-phosphonium bromide

A mixture of methyl-10bromodecanoate (5.22 g), triphenylphosphine (7.74 g) and sodium iodide (0.3 g) in acetonitrile (50 ml) was refluxed for 24 hours.

The acetonitrile was evaporated in vacuo, the gummy residue dissolved in a minimum of dichloromethane, and diethyl ether added until the solution became cloudy. After cooling to 5° C. the solvents were decanted from the semi-solid material, which was washed several times with diethyl ether to give the product as a light-amber oil.

5-{3-[14-Methoxycarbonyl-(E)-1,2-oxidotetradeca(-3E),(5Z)dienyl]-phenyl}-2-triphenylmethyltetrazole To a suspension of 9-methoxycarbonylnonyltriphenylphosphonium bromide (1.09 g) in dry tetrahydrofuran (30 ml) under nitrogen at −70° C. (dry ice-/acetone) was added n-butyl lithium (1.29 ml of 1.6 molar solution in hexane). The reaction mixture was allowed to warm to room temperature, recooled to −70° C., and a solution of 1-[3-(2-triphenylmethyltetrazol-5-yl)phenyl]-1,2-oxido-pent-3-enal (0.83 g) in dry tetrahydrofuran (10 ml) added. The reaction mixture was allowed to warm to room temperature and stirred for 2 hours.

The reaction mixture was filtered, the filtrates evaporated in vacuo, and the residue triturated with diethylether several times. The ether extracts were reduced in volume and subjected to column chromatography (silica; eluant diethylether/hexane/triethylamine=50/50/0.1), finally giving the title compound as a yellow oil. (The compound was stored as an ether solution of known concentration under nitrogen at −20° C.)

(1S,2R)-5-{3-[2-(2-Methoxycarbonylethylthio)-1-hydroxy-14-methoxycarbonyl-tetradeca(3E),(5Z-)dienyl]phenyl}-2-triphenylmethyltetrazole To 5-{3-[14-methoxycarbonyl-(E)-1,2-oxido-tetradeca-(3E),(5Z)dienyl]-phenyl}-2-triphenylmethyltetrazole under nitrogen was added a solution of methyl-3-mercaptopropionate (92 mg) and triethyanine (106 µl) in dry methanol (0.5 ml) also under nitrogen. Further triethylamine (300 µl) was added to give an homogeneous reaction system. Then the reaction mixture was stirred at room temperature under nitrogen for 48 hours.

The reaction mixture was evaporated under nitrogen and purified by column chromatography (silica; eluant diethyl ether/hexane=1/1) to give the product as a yellow oil.

(1S,2R)-5-{3-[2-(2-Carboxyethylthio)-1-hydroxy-14-carboxy-tetra
deca(3E),(5E)dienyl]-phenyl}(-1H-tetrazole (1S,2R)-5-{3-[2-(2-Methoxycarbonylethylthio)-1-hydroxy-14-methoxycarbonyl-tetradeca(3E),(5Z-)dienyl]-phenyl-}2-triphenylmethyltetrazole (100 mg) was dissolved in a mixture of diethyl ether (4 ml), 98% formic acid (2 ml) and water (2 ml) and stirred at room temperature under nitrogen for 16 hours.

The reaction mixture was evaporated in vacuo to a gummy solid which was redissolved in tetrahydrofuran (1 ml) and 1 molar lithium hydroxide (800 μl), and stirred at room temperature for 48 hours.

After evaporating the tetrahydrofuran in vacuo the residual aqueous phase was washed with diethyl ether (2×), acidified to pH4 (2M hydrochloric acid) and extracted with chloroform (4×). After removal of the chloroform the residual oil was partially purified by preparative reverse phase HPLC to remove the predominant (3E,5Z) isomer and give the title compound as a light-yellow oil.

NMR δ d4-methanol (300 MHz). The spectrum showed a 4:1 mixture of the trans-trans and cis-trans isomers: 1.25 (multiplet, 12H), 1.55 (quintet, 2H), 2.03 (quartet, 2H), 2.26 (triplet, 2H), 2.49 (multiplet, 2H), 2.64 (multiplet, 2H), 3.65 (double doublet, 1H), 4.80 (doublet, 1H), ~5.5 (multiplet, 2H), ~6.0 (multiplet, 2H), ~7.4 (multiplet, 2H), 7.98 (multiplet, 1H), 8.00 (multiplet, 1H).

EXAMPLE 3

10-Bromo-1-decanol

A solution of 1,10-dihydroxydecane (80 g) in 47% hydrobromic acid (650 ml) was stirred at 80° C. whilst being continuously extracted with petroleum ether (boiling range 80°-100° ), for 24 hours.

The organic extracts were neutralised with solid potassium carbonate, filtered, and the filtrates evaporated to dryness. The resultant dark oil was fractionally distilled (Vigreaux apparatus) to give a colourless oil, boiling point 102°-104° (0.01 mm Hg). Part of this oil (52 g) was purified by preparative HPLC (silica; eluents:- diethyl ether/hexane 1:1) to remove a significant 1,10-dibromodecane impurity, finally yielding the title compound as a colourless oil.

10-Hydroxy-n-decyltriphenylphosphonium bromide

A solution 10-bromodecanol (23.7 g) and triphenylphosphine (78.6 g) in dry acetonitrile (100 ml) was refluxed for 48 hours.

The acetonitrile was evaporated in vacuo and the residual sticky white solid triturated with diethyl ether until granular. The product was dried by dissolving it in toluene and refluxing under a Dean and Stark apparatus for 24 hours. Evaporation of the toluene gave the product as a white crystalline solid (softens ~80° C.) (stored in a vacuum dessicator).

5-{3-[15-Hydroxy-(E)-1,2-oxido-pentadeca(3E),(5Z-)dienyl]-phenyl}-2-triphenylmethyltetrazole To a suspension of 10-hydroxy-n-decyltriphenylphosphonium bromide (11.98 g) in dry tetrahydrofuran (200 ml) under nitrogen at −70° C. (dry ice/acetone bath) was added n-butyl lithium (15 ml of 1.6 molar solution in hexane). (A light yellow colour was generated.) The mixture was allowed to warm to room temperature (colour deepening to orange) then re-cooled to −70° C. and a solution of 1-[3-(2-triphenylmethyltetrazol-5-yl)-phenyl]-1,2-oxido-pent-3-enal (9.68 g) in dry tetrahydrofuran (100 ml) added. The reaction mixture was allowed to warm to room temperature (disappearance of orange colour) and stirred for a further 2 hours.

The tetrahydrofuran was removed in vacuo and the residual sticky liquid dissolved in dichloromethene 1% triethylamine (100 ml), hexane (20 ml) added, and the cloudy solution stored at 0°-5° C. over night. The precipitated solid was removed by filtration, the solvents removed in vacuo, and the residue redissolved in dichlorormethane 1% triethylamine (30 ml) and subjected to column chromatography (silica; eluent diethyl ether 0.5% triethylamine) to yield the title compound as a yellow foam-like solid.

(1S,2R)-5-{3-[2-(2-Methoxycarbonylethylthio)-1,15-dihydroxypentadeca(3E),(5Z)dienyl]-phenyl}-2-triphenylmethyltetrazole To 5-{3-[15-hydroxy-(E)-1,2-oxido-pentadeca(3E),(5Z)-dienyl]-phenyl}-2-triphenylmethyltetrazole (5.4 g) under nitrogen was added a solution of methyl-3-mercaptopropionate (1.04 g) and triethylamine (2.4 ml) in dry methanol (20 ml) also under nitrogen. The reaction mixture was then stirred under nitrogen at room temperature for 48 hours.

The volatiles were evaporated under a nitrogen stream and the residual oil purified by column chromatography (silica; eluents (i) diethyl ether:hexane=3:1 (ii) 100% diethylether) to give the product as a white foam.

(1S,2R)-5-}3-[2-(2-Carboxyethylthio)-1,15-dihydroxypentadeca-(3E),(5Z)-dienyl]-phenyl}-1H-tetrazole A solution of (1S,2R)-5-{3-[2-(2-methoxycarbonylethylthio)-1,15-dihydroxypentadeca(3E),(5Z)dienyl]-phenyl}-2-triphenylmethyltetrazole (2.75 g) in diethylether (40 ml), 98% formic acid (20 ml) and water (20 ml) was stirred under nitrogen at room temperature for 16 hours.

The reaction mixture was evaporated to dryness, the residue redissolved in methanol (20 ml) and 2 molar potassium carbonate (8 ml) added. The resulting suspension was stirred under nitrogen at room temperature for 48 hours.

The methanol was removed in vacuo, the aqueous phase washed with diethylether, acidified with 2M hydrochloric acid and extracted with chloroform to give the title compound as a yellow foam.

NMR δ d4-methanol (300 MHz). The spectrum showed a 3:1 mixture of the cis-trans and trans-trans isomers: 1.25 (multiplet, 12H), 1.52 (quintet, 2H), 2.08 (quartet, 2H), 2.53 (multiplet, 2H), 2.63 (multiplet, 2H), 3.53 (triplet, 2H), 3.68 (doublet doublet, 1H), 4.86 (doublet, 1H), 5.36 (doublet of triplets, 1H, J=10 Hz), 5.63 (double doublet, 1H, J=16 Hz), 5.97 (triplet, 1H, J=10 Hz), 6.27 (double doublet, 4H, J=16 Hz), 7.53 (2 ortho couplings, 1H), 7.56 (1 ortho, 2 meta couplings, 1H), 7.92 (1 ortho, 2 meta couplings, 1H), 8.02 (2 meta couplings, 1H).

The active compounds of the invention are preferably employed in salt form. The following formulations are given by way of example:

EXAMPLE 4

Soft gelatin capsule

Each soft gelatin capsule contains:

| Active ingredient | 150 mg |
|---|---|
| Arachis oil | 150 mg |

After mixing together, the blend is filled into soft gelatin capsules using the appropriate equipment.

EXAMPLE 5

Hard Gelatin capsule

Each capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 6

Aerosol

| Active ingredient | 10 mg |
|---|---|
| Ethanol | 50 mg |
| Dichlorodifluoromethane (Propellant 12) | 658 mg |
| Dichlorotetrafluoroethane (Propellant 114) | 282 mg |

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 or 100 μl equivalent to 0.5–1 mg active ingredient.

We claim

1. A compound of the formula

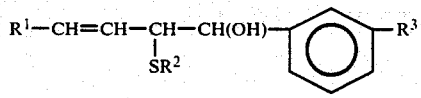

in which $R^1$ is (i) $R^4O(CH_2CH_2O)_n(CH_2)_m$—where $R^4$ is hydrogen or $C_{1-5}$ alkyl, n is 0 or 1 to 5 and m is 1 to 7, or (ii) $R^5$—X— where $R^5$ is $COR^8$, —OH, $NH_2$, tetrazolyl, —$SO_3H$ or —$PO_3H_2$, where $R^8$ is —OH, —O($C_1$-$C_4$alkyl) or —$NR^9R^{10}$, and $R^9$ and $R^{10}$ are independently H or $C_1$-$C_5$ alkyl and X is a $C_{6-20}$ alkylene or a $C_{6-20}$ alkenylene radical containing from 1 to 3 double bonds, $R^2$ is a group of the formula A—B— where A is —COOH, —COO($C_{1-4}$ alkyl), or

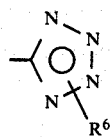

where $R^6$ is hydrogen and B is $C_{1-6}$ alkylene, and $R^3$ —COOH, —COO($C_{1-4}$ alkyl), or

where $R^7$ is hydrogen or a pharmaceutically acceptable base addition salt thereof.

2. A compound according to claim 1 in which $R^1$ is $R^4O$ ($CH_2CH_2O)_n(CH_2)_m$—is 2 to 4 and n is 1 to 3 and $R^4$ is $C_{1-5}$ alkyl.

3. A compound according to claim 1 in which $R^1$ is $R^5$—X—, $R^5$ is —OH or $COR^8$ where $R^8$ is —OH or —$NR^9R^{11}$ and $R^9$ and $R^{10}$ are each hydrogen or $C_{1-4}$ alkyl, and X is —$(CH_2)_q$—CH=CH— or —$(CH_2)_r$CH=CHCH$_2$(CH=CH)$_2$— where q is 6 to 12 and r is 2 to 8.

4. A compound according to claim 1 of the formula

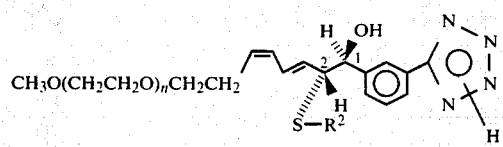

in which in n is 2 or 3, $R^2$ is —$(CH_2)_s$—A where A is COOH, COO($C_{1-4}$ alkyl) or

and s is 1, 2 or 3; and pharmaceutically acceptable salts thereof.

5. A compound according to claim 1 of the formula

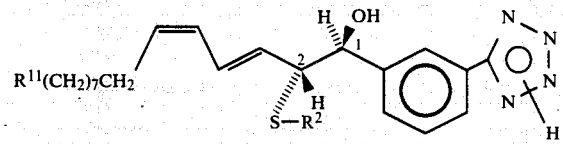

in which $R^{11}$ is —$CH_2OH$—COOH,—COO($C_{1-14}$ alkyl) or —$CONR^9R^{10}$ where $R^9$ and $R^{10}$ are hydrogen or $C_{1-14}$ alkyl, $R^2$ is —$(CH_2)_s$—A where A is —COOH or

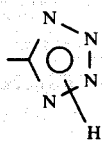

and s is 1, 2 or 3; and pharmaceutically acceptable salts thereof.

6. (1S,2R)-5-{3-[2-(2-Carboxyethylthio)-1,15-dihydroxypentadeca-(3E),(5Z)-dienyl]-phenyl}-1H-tetrazole.

7. A pharmaceutical formulation comprising a compound according to claim 1 in association with a pharmaceutically-acceptable diluent or carrier.

8. A method of treating a mammal, including a human, suffering from or an allergic disorder, which comprises administering to the mammal an effective amount of a compound as defined in claim 1.

* * * * *